(12) United States Patent
Feller

(10) Patent No.: US 7,201,065 B1
(45) Date of Patent: *Apr. 10, 2007

(54) ACOUSTIC FLOW SENSOR

(76) Inventor: Murray F Feller, 21577 NW. 75th Avenue Rd., Micanopy, FL (US) 32667

(*) Notice: Subject to any disclaimer, the term of this patent is extended or adjusted under 35 U.S.C. 154(b) by 42 days.

This patent is subject to a terminal disclaimer.

(21) Appl. No.: 11/163,164

(22) Filed: Oct. 7, 2005

Related U.S. Application Data

(63) Continuation-in-part of application No. PCT/US05/31647, filed on Sep. 7, 2005, which is a continuation-in-part of application No. 11/161,135, filed on Jul. 25, 2005, now Pat. No. 7,044,000, which is a continuation-in-part of application No. 10/946,834, filed on Sep. 22, 2004, now Pat. No. 6,973,842.

(51) Int. Cl.
*G01F 1/66* (2006.01)
(52) U.S. Cl. ............... 73/861.27; 73/597; 73/610
(58) Field of Classification Search ............... None
See application file for complete search history.

(56) References Cited

U.S. PATENT DOCUMENTS 6,973,842 B1 * 12/2005 Feller ............... 73/861.27
7,044,000 B2 * 5/2006 Feller ............... 73/861.27

OTHER PUBLICATIONS

Lynnwood, Lawrence C., Ultrasonic Measurements for Process Control, 1989, pp. 292-294 and related bibligraphic citations, Academic Press Inc., San Diego CA.

* cited by examiner

*Primary Examiner*—Harshad Patel
(74) *Attorney, Agent, or Firm*—David Kiewit

(57) ABSTRACT

A fluid flow sensor uses pairs of acoustic transducers to generate quasi-helical acoustic beams reflected multiple times from an inside surface of a pipe. The transducers are arranged so that each two pairs generate counter-rotating beams. When fluid flowing in the pipe has both a rotary and an axial flow component the rotary component adds to the apparent flow rate measured in one rotational direction and subtracts from that measured in the other. Hence, a combination of transit time measurements along the two paths can be used to cancel out the effects of the rotary flow component and yield a measure of the rate of flow along the pipe axis. In some cases multiple probes are used to increase the amount of flowing fluid that is sampled.

10 Claims, 5 Drawing Sheets

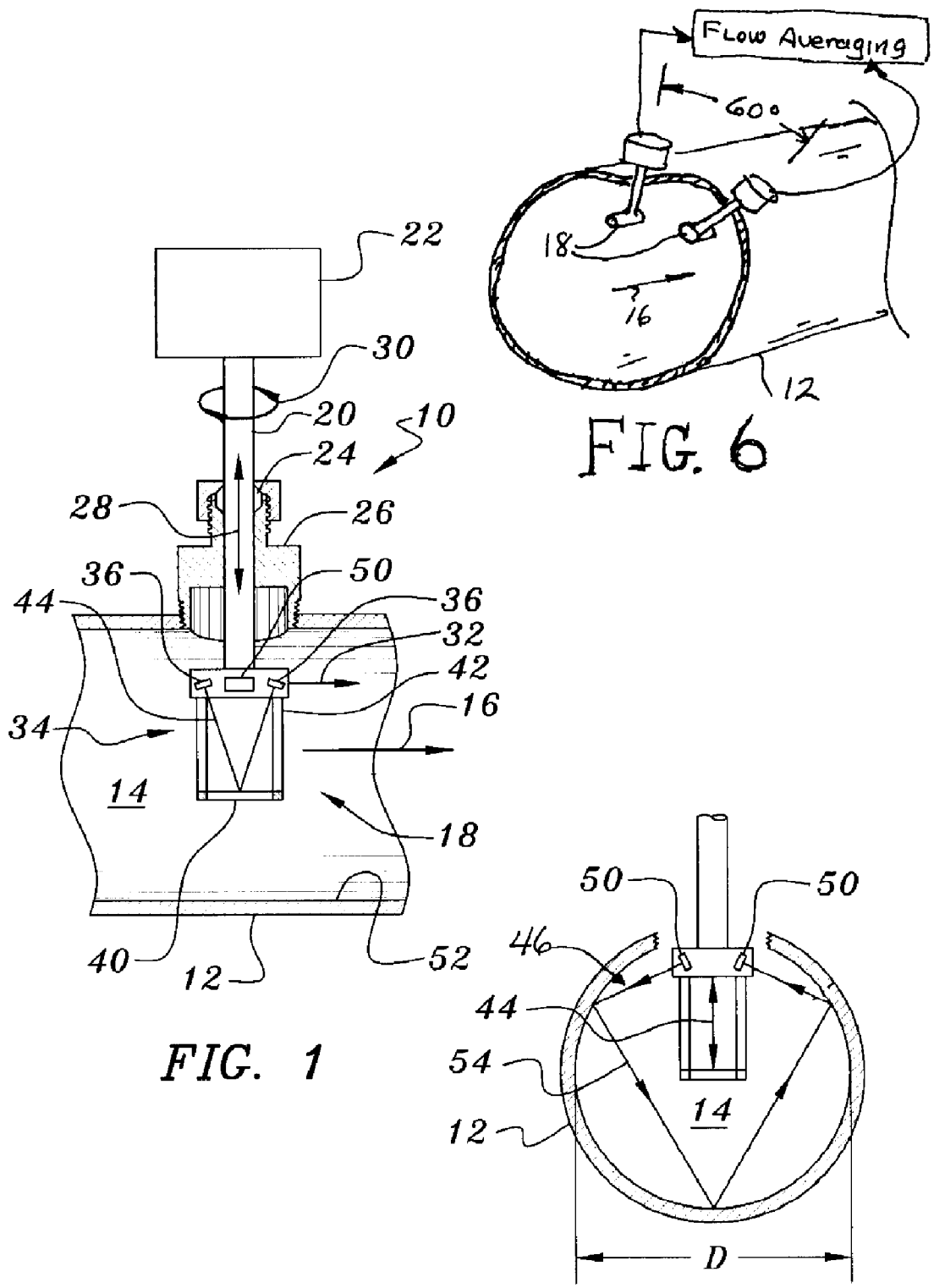

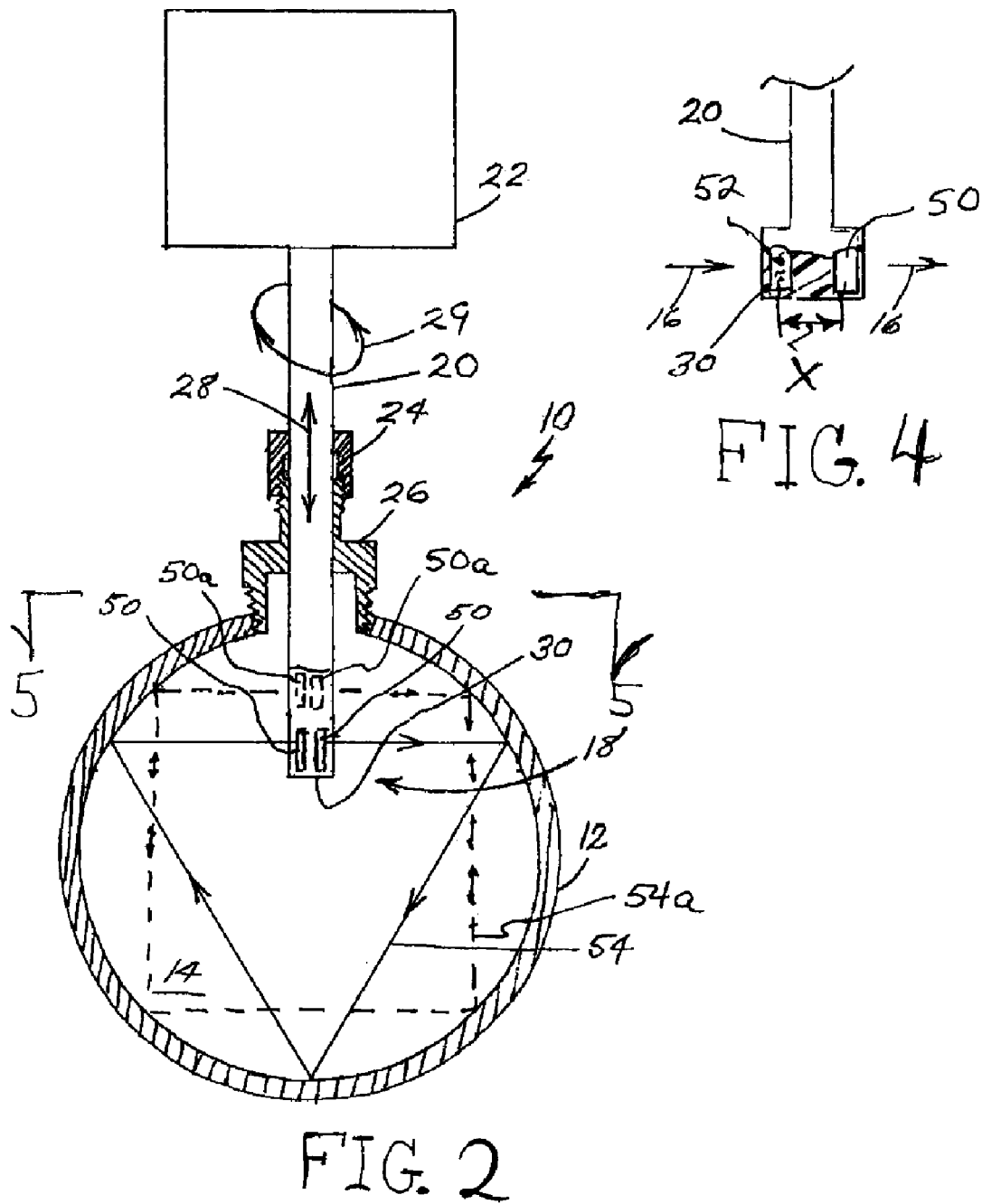

ACOUSTIC FLOW SENSOR

This application is a continuation-in-part of PCT application PCT/US05/31647, filed 7 Sep. 2005, which is a continuation-in-part of U.S. application Ser. No. 11/161,135, filed 25 Jul. 2005 now U.S. Pat. No. 7,044,000, which is a continuation-in-part of U.S. patent application Ser. No. 10/946,834, filed 22 Sep. 2004 now U.S. Pat. No. 6,973,842.

BACKGROUND

The present invention relates to acoustic apparatus and methods for fluid flow measurement. More specifically, it relates to apparatus and methods for compensating for variations in the internal diameters of pipes in which flow is measured, for measuring flow in the presence of flow rotation or other profile variations, for optimizing the location and orientation of a flow sensor and for detecting accumulation of pipe wall deposits.

The present invention relates to apparatus and methods of compensating for the variation of internal diameters of pipes in which sensing probes are inserted, optimizing their insertion depth and orientation during installation, and detecting the accumulation of pipe wall deposits.

Insertion probes for detecting the flow of fluids are typically mounted in round pipes having internal diameters that are not precisely known. Because these probes are generally used to measure flow rate by sampling a small portion of the flow profile and deriving from that measurement the volumetric flow rate based upon an assumed internal pipe diameter, a pipe diameter different from that assumed can introduce significant error into the derived results. The magnitude of the problem can be seen by considering the ASTM A 106 dimensional limits for a range of diameters about a nominal diameter of six inches for Schedule 40 steel pipe. The tolerances are +1/16", −1/32" in diameter and +15%, −12.5% in wall thickness. The corresponding variation in wetted cross sectional area approaches 2% and provides that degree of uncertainty in determining volumetric flow rate. Those skilled in the art will recognize that tolerances vary with the pipe size and may increase or decrease from the recited example.

Insertion probes generally need to be inserted to a correct depth and to have a precise angular orientation with respect to the direction of the flowing fluid in order to minimize flow measurement error. Feldman et al., in U.S. Pat. No. 6,584,860, teach methods of and apparatus for measuring a distance between a portion of the piping apparatus into which a probe is inserted, and for combining the results of these measurements with a presumed pipe diameter in order to insert the probe to the correct depth.

SUMMARY OF THE INVENTION

In a preferred embodiment of the present invention, a probe type acoustic time-of-flight (also known as transit-time) flow sensor provides both flow rate and pipe size measurement. A probe of this sort comprises a transmitting transducer arranged to generate an acoustic beam directed so as to make a plurality of reflective contacts with the pipe's interior wall prior to reaching a receiving transducer displaced along the flow axis from the transmitting transducer. This displacement enables a flow rate related time measurement to be made. The preferred transducers may periodically exchange functions or may concurrently be in the transmitting and receiving modes to measure a differential acoustic transit-time between the upstream and downstream acoustic signals and therefore the flow rate. Each of the preferred transducers is aimed to project an acoustic energy beam at an angle which crosses the flow axis so that, after being reflected by the pipe walls, the beam can be received by the other transducer. The acoustic energy paths between a pair of transducers thus define a quasi-helix having acoustic energy flowing along it in both of two directions.

The acoustic energy paths of this embodiment, when projected onto a cross-section perpendicular to the axis of the pipe, approximate chordal paths. In a preferred version of the second embodiment of the present invention, where the insertion depth of the transducers is 25% of the pipe's diameter and the transducers are beamed horizontally, these paths define a quasi-helix that appears, in cross-section, like an equilateral triangle. That is, the path can conceptually be constructed by drawing an equilateral triangle, cutting through one vertex and then moving the cut ends of the triangle apart along a line perpendicular to the plane of the triangle by a selected amount corresponding to a flow measurement distance between the two transducers. The associated transit time is responsive to the flow rates along those paths and the fluid flow intersecting those paths provides an approximation of the volumetric flow in the entire pipe. Hence, the volumetric accuracy is improved. Further improvement is possible when more than one probe is used and is particularly effective when the respective associated acoustic energy paths have different locations in the pipe cross-section. Such improvement is particularly evident when the flow profile is not uniform.

A particular preferred embodiment of the invention provides compensation for the effects of rotating flow components. Because the quasi-helical path lengths used in the second embodiment discussed above can be much greater than the distance along the pipe axis by which a pair of transducers is spaced apart, any non-axial (i.e. rotary) component of flow (e.g., as may be introduced by a bend in the piping upstream of the measurement location) can introduce errors into the measurement. These errors can be canceled out by incorporating a second pair of transducers on a the same or a different probe head, where the second pair of transducers is arranged to generate a quasi-helical acoustic beam in the opposite rotation direction from that defined by the first pair of transducers. That is, a first pair of acoustic transducers spaced apart along the axis of the pipe defines a first acoustic beam that is reflected at least twice from an internal surface of the pipe, and that follows a path from an upstream one of the transducers to the downstream one that, when viewed along the axis of the pipe in the flow direction, is a clockwise quasi-helix. A second pair of acoustic transducers is similarly arranged to define a counter-clockwise quasi-helical path. In an arrangement of this sort, both pairs of transducers would have essentially the same response to an component of flow in the axial direction, but would have equal and opposite responses to a rotary component of flow. Thus, adding the two signals would act to remove the effects of the rotary component from the overall flow signal.

The accuracy of a flow probe measurement is enhanced by increasing the fraction of the overall flow that is sampled by the instrument. In some embodiments of the invention multiple probes are used and each probe axis has a respective angular setting with respect to the pipe axis. In arrangements of this sort each of the probes comprises a respective sensing head having at least one pair of transducers mounted on it in order to sample respective portions of the pipe so that a greater fraction of the overall flow is sampled For any of the above described embodiments the magnitude of the signal detected by the receiving transducer of the acoustic distance measuring device is an indication of both the optimization of the acoustic path and of possible presence of scale or other internal deposits. Thus, changes in signal level over time may provide a means of monitoring the build up in internal deposits.

Although it is believed that the foregoing recital of features and advantages may be of use to one who is skilled in the art and wishes to learn how to practice the invention, it will be recognized that the foregoing recital is not intended to list all of the features and advantages of the invention, and that less than all of the recited features and advantages may be provided by some embodiments.

BRIEF DESCRIPTION OF DRAWINGS

The various advantages of the present invention will become apparent to one skilled in the art by reading the following specification and subjoined claims and by referencing the following drawings in which:

FIG. 1 is a partly schematic vertical sectional view, taken along an axis of a pipe, of an insertion probe having separate pairs of transducers for measuring pipe size and flow rate.

FIG. 2 is a partly schematic, partly sectional view taken perpendicular to the axis of the pipe of a preferred embodiment of an insertion probe using a single pair of transducers at two depths to measure both pipe size and flow rate.

FIG. 3 is a partial sectional view depicting an alternate acoustic measurement path defined by one or more angled transducers.

FIG. 4 is a detailed partly cut-away view of the probe of FIG. 2 taken along the axis of the pipe.

FIG. 6 is a partly schematic, partly cut-away view of two flow probes oriented at different angular settings with respect to the flow axis.

DETAILED DESCRIPTION

Figure 7:
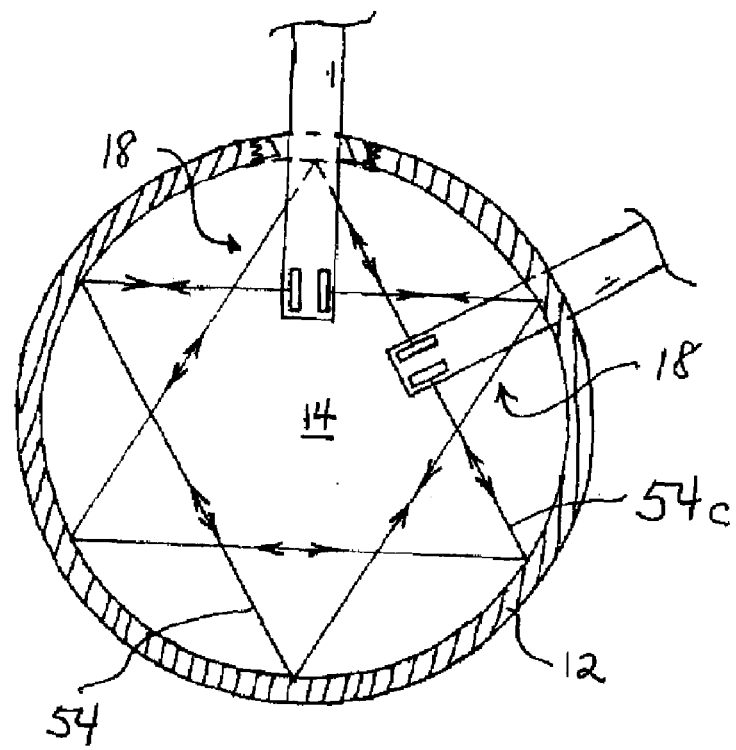
FIG. 7 is a partly schematic, partly sectional view taken perpendicular to the axis of the pipe of the embodiment of FIG. 6.

In studying the detailed description, the reader may be aided by noting definitions of certain words and phrases throughout this patent document. Whenever those definitions are provided, those of ordinary skill in the art should understand that in many, if not most instances, such definitions apply to both preceding and following uses of such defined words and phrases. At the outset of this Description, one may note that the terms "include" and "comprise," as well as derivatives thereof, mean inclusion without limitation; and the term "or," is inclusive, meaning and/or.

The term "insertion probe" as used herein, denotes an item elongated along a probe axis and designed to be inserted into a pipe or other vessel so that a sensing element on, or closely adjacent, the inserted end of the probe is at a selected probe axial insertion depth and orientation with respect to that pipe or vessel. Although much of the ensuing discussion is directed toward in-field insertion of probes into a pre-existing pipe, it will be understood that an insertion probe could equally well be factory-installed in a pipe section that was then built into a run of piping. A "flow probe", as used herein, provides the conventional denotation of a portion of a flow sensor configured to be inserted into a pipe. A "flow velocity detector", as used herein, is any sort of device (including, but not limited to a device in which a single transducer pair senses both flow velocity and pipe size) mounted on a flow probe to provide an electrical signal output (hereinafter "raw flow signal") that is a measure of the rate at which fluid flows along a predetermined "flow measurement direction" defined with respect to the flow probe. When the flow probe is inserted into a pipe so that the flow measurement direction is parallel to or co-linear with an axis of the pipe, the raw flow signal is then a measure of the rate at which fluid is flowing past the probe at whatever insertion depth has been selected. In many cases what is desired is the volumetric flow rate (e.g., gallons per minute flowing through the pipe), which is calculated by multiplying a representative fluid flow rate by the cross-sectional area of the inside of the pipe. Thus a "volumetric flow sensor" is an instrument providing an output signal value representative of the volumetric flow rate, which may be described as a respective volumetric flow rate when derived from phase changes in upstream and downstream acoustic transmissions between a pair of transducers, or which may be referred to as a composite volumetric flow rate when generated by combining (e.g., by averaging) measurements made using multiple pairs of transducers.

A portion of the ensuing disclosure will describe apparatus operated to define acoustic beams traveling along paths comprised of straight line segments skewed with respect to the pipe axis. Those versed in geometry will appreciate that in a limiting situation in which the individual straight line segments have infinitesimal length the path becomes a helix. Hence, acoustic paths described herein will be referred to as having a quasi-helical shape. These quasi-helical acoustic beams are sometimes described as being propagated transverse to the pipe axis from a transducer. The reader will appreciate that in this context 'transverse' describes both beams having a center line perpendicular to the pipe axis and beams that are angled away from the perpendicular so that the center line of the beam extends between two transducers that are spaced apart along the pipe axis.

Several embodiments of the invention are depicted in the various figures of the drawing. A common setting for the drawing shows a transducer probe inserted through a probe insertion fitting extending upwards from the top of the pipe as a matter of convenience. Those skilled in the art will recognize that other insertion orientations may equally well be used. Moreover, directional terms such as "up" and "down" in the subsequent disclosure are used with reference to the depicted orientation in the interest of more clearly explaining the invention, and are not to be taken as limiting the invention to any particular setting.

In large pipes having a smooth inside surface one commonly finds that a flow velocity detector inserted to 11% of the ID of the pipe will provide a representative raw flow signal output value usable for determining volumetric flow over a wide range of flow rates. In smaller pipes or those having a rough internal surface, a somewhat deeper insertion depth is typically desired for best volumetric accuracy. Thus, regardless of what insertion depth is nominally selected, it will be understood that installation of a flow probe comprises both inserting the probe to a selected insertion depth and assuring that the predetermined flow measurement direction is parallel to the pipe axis. Furthermore, these insertion depths assume a typical flow velocity profile through the pipe as is found when there is a length of straight pipe, both upstream and downstream of the flow sensor location, that is much greater than the pipe diameter, or when aggressive flow conditioning methods are used to achieve the same result. This can cause a problem in that many applications require the sensor be located close to an elbow, valve or branched connection which, over a range of fluid velocities, can so distort the velocity profile at the flow sensor location as to make the conventional flow probe measurement useless.

Turning now to FIGS. 1–3, one finds various acoustic time-of-flight flow insertion probe sensors 10 in accordance with a first embodiment of the invention mounted in a pipe 12 containing a fluid 14 flowing along the pipe axis, indicated with the arrow 16. As is conventional in the use of insertion probes, the depicted sensing head 18 is supported by a hollow stem 20 serving as a conduit for wires (not shown) coupling the sensing head 18 to associated circuitry 22 that is conventionally external to the pipe.

During installation of a preferred probe sensor 10 the shaft seal 24 of a conventional insertion fitting can be loosened to allow an operator to move the stem 20 into and out of the pipe, as depicted by the double-headed arrow 28, and to rotate the stem about its axis, as depicted by the double headed arrow 29, into a selected setting. As will be discussed in greater detail later hereinafter, these adjustments can assure that the sensing head 18 is disposed at a desired insertion depth and that the flow measurement direction is parallel to or coincident with the flow axis 16. Those skilled in the flow measurement arts will recognize that many mechanisms and approaches can be used to adjust both the depth and the rotational settings.

In some embodiments of the invention, as depicted in FIGS. 1 and 2, a pipe size sensor 46 is used with a separate flow rate detector 34, which may be of the ultrasonic transit-time type. An exemplar flow rate detector of this sort comprises a pair of flow-measuring piezoelectric transducers 36 aimed through the fluid 14 at a reflector 40 supported at a selected distance by suitable support members 42 so as to define a flow-measuring acoustic transit time path 44 that, when the angular setting of the probe is at the desired value, lies in a plane containing the axis 16 of the pipe. The separate pipe size detector 46 employs transit-time measurements to accurately determine the inside diameter (shown as "D" in FIG. 3) of the pipe 12. It should be clear that any type of flow detector that is compatible with probe mounting can be used with the pipe size detector 46 and that these include, but are not limited to, turbine sensors, moving target sensors, and electromagnetic or Faraday sensors.

A pipe size detector of the invention, as noted above, is operable to yield a transit time output from which the diameter D of the pipe 12 can be calculated. In an embodiment depicted in FIGS. 1 and 3 the detector comprises a pair of size-measuring transducers 50 disposed on the sensing head 18 and oriented so as to generate an acoustic size-measuring beam perpendicular to the flow measurement direction 32. During operation of an exemplar pipe size detector, one of the transducers 50 projects a short burst of ultrasonic energy, which may comprise sixteen cycles of a 4 MHz signal, along a multi-segment path 54 toward the wall of the pipe. When placed in a pipe full of fluid, the acoustic beam can be reflected multiple times from an internal surface 52 of the pipe 12 to define a complete acoustic path 54, the total length of which can be derived immediately from a measurement of the transit time. Those skilled in the acoustic arts will recognize that the multi-segment path 54 is depicted, in the interest of clarity of presentation, as a single line—i.e., the center line of the beam—and that dispersion of the beam about the center line is ignored.

In one experimental embodiment the transducers 50 were oriented to transmit and receive initially horizontal acoustic beams reflected three times from the inner surface 52 of the pipe. In a pipe 12 having a conventional round cross section, these transducers 50 are depicted as having an insertion depth of 25% of the pipe diameter, D. This provides an acoustic path 54, which essentially formed an equilateral triangle in a plane transverse to the axis of the pipe. As noted previously, many other path geometries are possible, and tests have shown that a four-reflection "square" path 54a between transducers 50 oriented perpendicular to the probe axis at an insertion depth of 13.3% of the pipe ID also provides good results by using a substantially longer path with one more reflection than is found when the triangular path is used.

Figure 5:
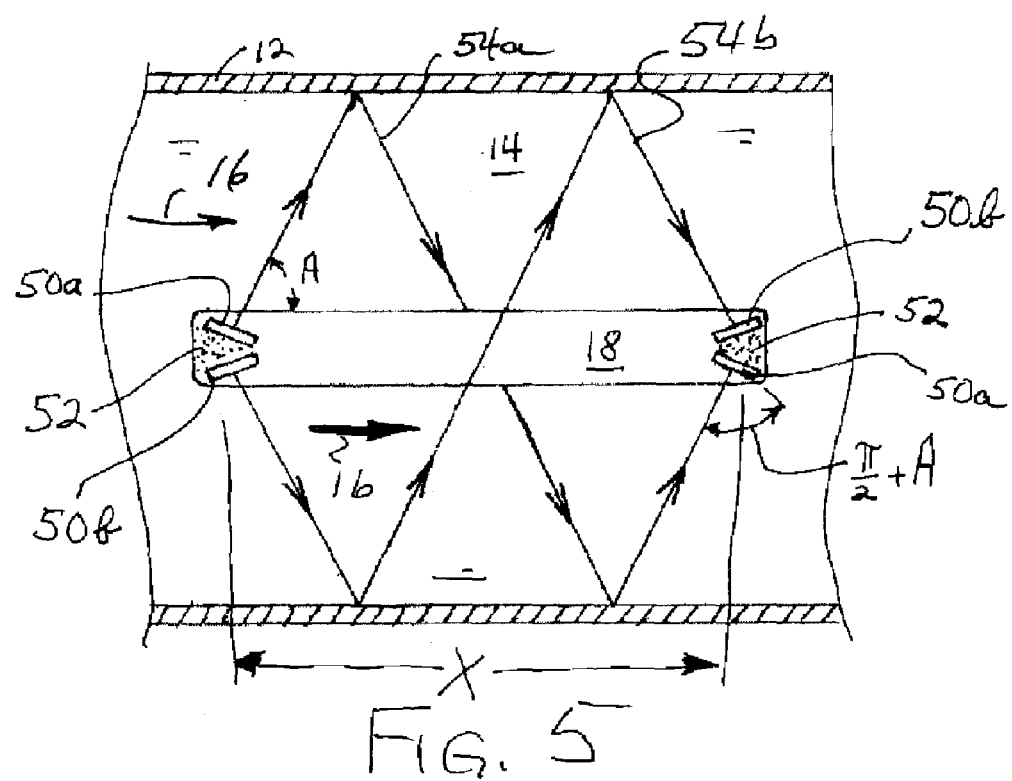
FIG. 5 is an axial sectional view of a probe head having two pairs of transducers for generating associated quasi-helical beams in both of two possible directions of rotation.

Turning now to FIG. 2 one finds a depiction of a preferred sensor in which a single pair of piezoelectric transducers 50 is used to measure both flow velocity and pipe size. In this embodiment the sensing head 18 comprises a pair of piezoelectric transducers 50 mounted in a suitable support 30, spaced apart along the flow measurement direction as indicated in FIGS. 4 and 5, and aimed transverse to the pipe axis through the fluid 14 at an inner surface of the pipe 12. The acoustic path 54, in these cases, forms a quasi-helix that, when viewed along the axis of the pipe, has the same appearance as the chordal paths described in the first embodiment—i.e., looks like an equilateral triangle or a square, depending on the selected insertion depth.

Although one of the motivations for combining the size and velocity measurement functions is to reduce the component count and complexity when compared with an embodiment using separate flow and size measurement devices, a single sensor head 18 of the invention may optionally be provided with two pairs of transducers 50, 50a spaced apart along the probe axis, each pair having its own associated acoustic path 54, 54a that can be used for measuring both the pipe ID and a respective volumetric flow rate. This approach, depicted in FIG. 2, allows for measurements to be made using additional acoustic paths that sample different portions of the overall flow profile and that can thus improve the overall accuracy of measurement when the respective diameter and volumetric flow rates are averaged, or otherwise combined, to yield a single, composite measurement of volumetric flow rate. Moreover, this approach provides redundancy which may offer increased system reliability.

Yet a further embodiment of the invention, as depicted in FIG. 6 and FIG. 7, employs multiple probes, where each probe axis has a respective angular setting with respect to the flow axis and where the probes are optionally spaced out along the pipe axis by selected probe-to-probe spacings. In arrangements of this sort each of the probes comprises a respective sensing head having at least one pair of transducers mounted on it in order to sample respective portions of the overall flow. In a preferred embodiment depicted in FIG. 7, each of the two sensing heads 18 generates a respective three-segment acoustic beam 54, 54c. These beams are separated by sixty degrees of arc about the flow axis, where the projected acoustic paths trace out a familiar Jewish star.

In a particular preferred embodiment two probes can be arranged to provide acoustic paths that differ primarily in being enantiomorphic. In the example depicted in FIG. 7, for example, one could chose one of the three-segment beams 54 to describe a clockwise path along the flow direction and the other 54c to describe a counterclockwise path. This, as discussed elsewhere in this disclosure, allows one to compensate for a rotary flow component. There is, of course, no general requirement for having nearly identical acoustic paths generated at each of the probes. One could, for example, use different insertion depths for each of two probes so that the first probe generated at three-segment quasi-helix and the second generated a four-segment quasi-helix. Moreover, the use of multiple probes spaced out along the flow axis does not preclude the use of additional pairs of transducers spaced apart along the probe axis of one or more of the probes. In order to prevent interference between pairs of transducers in an arrangement of this sort, one may space each probe out from the other probes along the pipe axis.

A flow measurement direction spacing, denoted as X in FIGS. 4 and 5, between the two transducers 50 in a pair thereof lies along the axis of flow when the probe is properly oriented. This ensures that the acoustic paths of interest are quasi-helices, and do not lie in a single plane. This flow measurement direction spacing is, of course, essential in order to enable a differential transit-time measurement of flow rate to be made. The transducers, particularly for small pipe sizes, may be angled off the exact perpendicular to the pipe axis in order to maximize the acoustic transmission along the lines 54 between the transducers. In the depiction of FIG. 5, one of the transducers is set to transmit and receive along a beam making an acute angle A with the flow measurement direction and the other of the transducers is set to transmit and receive along a beam making an obtuse angle, that is ninety degrees of arc greater than A, with that direction. Because the acoustic beams have an angular dispersion—i.e., are typically cones rather than straight lines—in some situations one may choose to set the transducers perpendicular to the flow measurement direction and select the flow measurement direction spacing and the angular dispersion so that off-axis components of the acoustic beams can propagate between the separated pair of transducers.

The transducers, as illustrated in FIG. 5, are preferably backed or partially surrounded by known acoustic isolation materials 52 such as a polymeric foam or a resonating material in order to minimize undesired acoustic radiation and reception.

During exemplary operation of an instrument providing both size and flow rate data, the transducers 50 concurrently transmit and receive short bursts of acoustic energy consisting of sixteen cycles of a 4 MHz signal along the multi-segment acoustic path lines 54. When placed in a pipe full of fluid, the acoustic beams are reflected multiple times from the internal surface of pipe 52 to define the complete acoustic path between the transducers from which one can immediately derive the transit time, from which the corresponding internal pipe diameter can be determined. The cyclic signals are compared, as is known in the art of transit-time flow meters, in order to derive the time difference between them from which fluid flow rate is determined.

The arrangements described above operate for selected combinations of transducer angles, rotational settings of the probe stem, insertion depths and pipe sizes and depend on these parameters being chosen so as to form a quasi-helical acoustic path having a quasi-helix axis parallel to or along the axis of the pipe. If the probe stem is at an incorrect angular setting the acoustic beams will generally follow an undesired path, so that a beam from one of the transducers is not received by the other. Correspondingly, if the insertion depth is slightly different than the selected one, the multiply reflected acoustic beams will largely miss the receiving transducer or transducers. The reader should recognize that there may be more than one insertion depth within a pipe at which a readily detectable signal will be found.

The requirement for precise positioning is a positive aid during installation of a sensing head of the invention. As the probe approaches the optimum location in both depth and rotational angle with respect to the central axis of the pipe, the magnitude of the received acoustic signals rapidly increases. The rate of change of these signals depends on several factors such as the beam angles, transducer alignment and condition of the pipe's reflective surface. In an implementation of the invention where the probe transducers were 0.200" wide, 0.125" high and 0.020" thick, and the probe was located in a circular section simulating a pipe having an eight inch ID, a probe insertion depth differing by about 0.050" from the optimum depth produced a received acoustic signal variation of 50%, thus providing the installer with a usable insertion depth tolerance value. A probe rotation of about 5 degrees from the optimum alignment with the central axis of the pipe also produced a received acoustic signal variation of 50%, similarly providing the installer with a rotational tolerance value. This order of sensitivity to mechanical positioning of the probe is, from the perspective of personnel installing the probe, a good balance for locating the approximate insertion position and then making fine adjustments for its optimization.

Although some portions of the foregoing discussion have described the use of a single pair of acoustic transducers for measuring flow rate and pipe size, a preferred embodiment, as depicted in FIG. 5 uses at least a second pair of transducers to compensate for the effects of rotating flow components. The quasi-helical path lengths discussed above can be much greater than the distance, X, along the pipe axis by which a pair of transducers is spaced apart. Hence, any non-axial component of flow (e.g., as may be introduced by a bend in the piping upstream of the measurement location) can introduce errors into a measurement made with a single pair of transducers. These errors can be canceled out by using two pairs 50a, 50b of transducers arranged to generate two quasi-helical acoustic beams 54a, 54b having opposite rotation directions. That is, if one were to look along the direction of flow 16 depicted in FIG. 5, the quasi-helical beam 54a, extending between the first pair of transducers 50a would appear as a left-handed screw, while the other beam 54b between the second pair 50b of transducers would appear as a right-handed screw. In an arrangement of this sort, both pairs of transducers would have essentially the same response to an component of flow in the axial direction, but would have equal and opposite responses to a rotary component of flow. Thus, adding the two signals would act to remove the effects of the rotary component from the overall flow signal. Those skilled in the measurement arts will recognize that many approaches may be used to handle the signals from the two oppositely directed rotational paths, and that these may comprise offsets and scale adjustments between the two pairs of transducers 50a, 50b. Moreover, there is no general requirement that the two associated pairs of transducers be on the same probe. In embodiments of the inventions using multiple probes, one could chose to have a first of two associated pairs of transducers on a first of the probes and that pair with which it is associated on a second probe, which may be disposed at a different angle to the axis of the pipe, as discussed with respect to FIG. 7.

Figure 8:
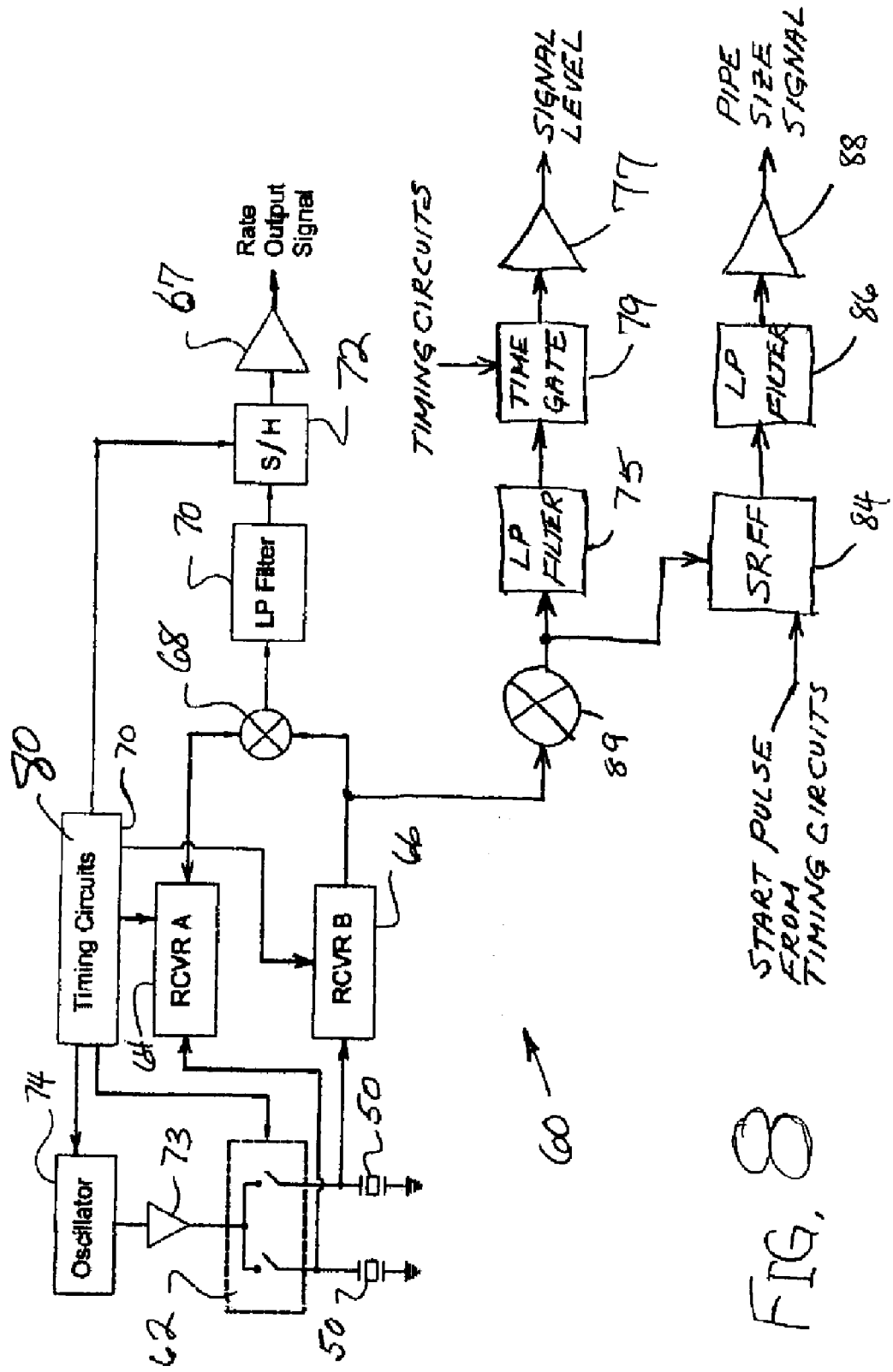
FIG. 8 is a simplified block diagram of a signal processing circuit of the invention.
Figure 10:
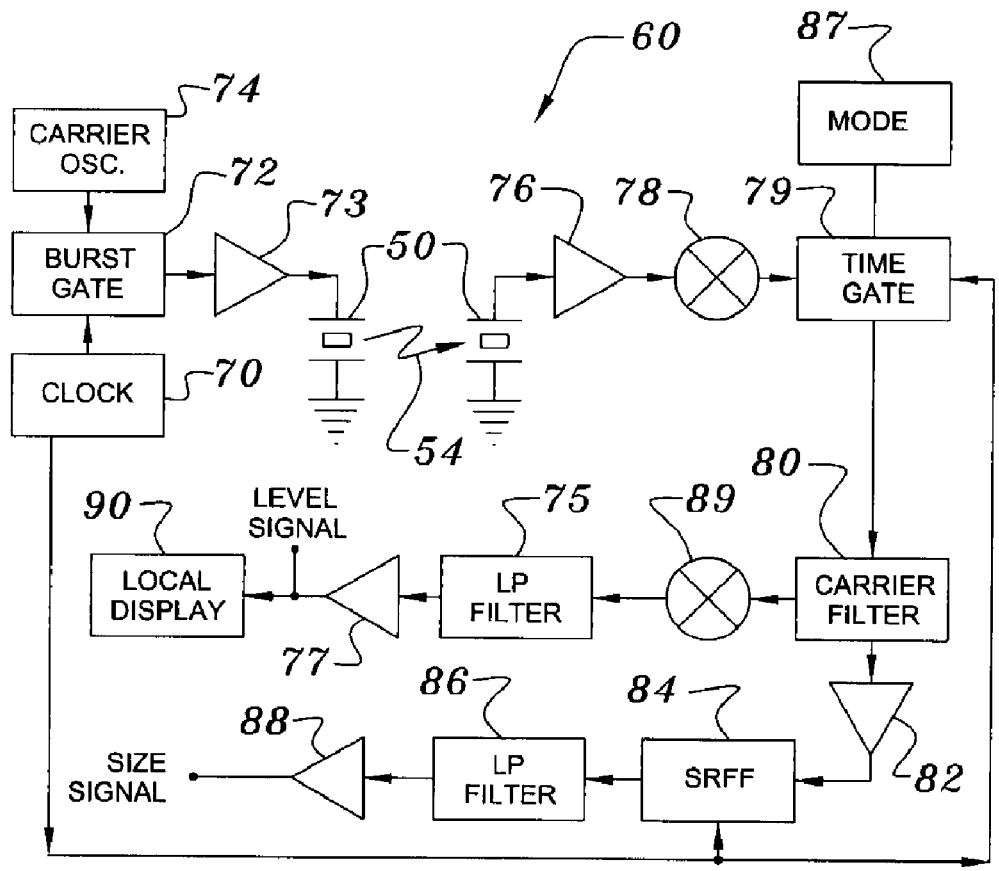
FIG. 10 is a simplified block diagram of a circuit for aiding installation, measuring pipe diameter, and measuring flow.
Figure 9:
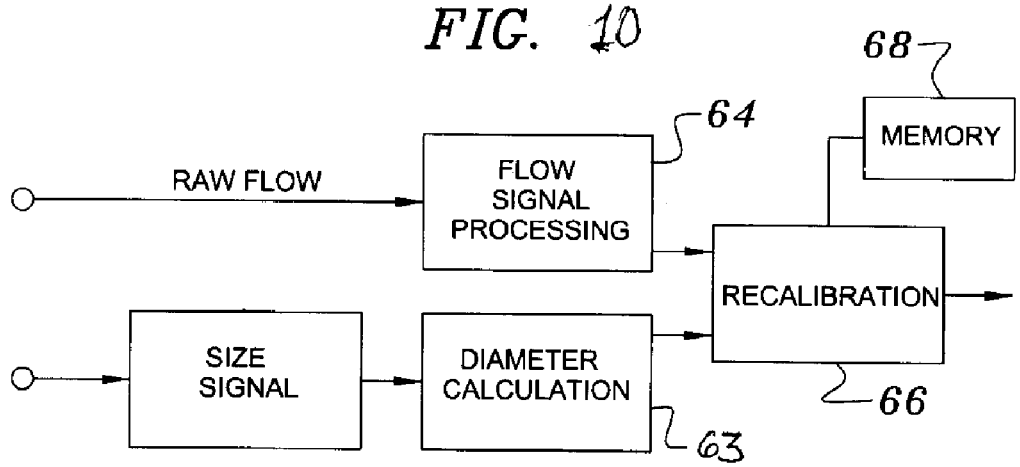
FIG. 9 is a flow chart of a process using an output from a separate size sensing circuit to calibrate a flow measurement.

Turning now to FIG. 8, one finds a block diagram of a simplified exemplary signal processing circuit 60 using the principles of both ultrasonic time-of flight flow rate detection and distance detection for the present invention. One portion of the circuit is used to provide a flow rate signal on an ongoing basis. Another portion is used to determine the actual pipe size. A third portion is used to determine optimal rotation of the probe about its axis and to set the probe to its desired depth. A similar presentation for embodiments in which separate pipe size and flow rate sensors are used is depicted in FIGS. 9 and 10. Moreover, it will be recognized that more than two pairs of transducers (e.g., two pairs of transducers on each of two different probes) may be used to generate the signals.

Although many different circuits have been used for transit-time measurement of flow, a preferred circuit providing for transit-time flow measurement, pipe size measurement and probe installation is depicted in FIG. 8 where an oscillator 74 produces bursts of continuous high frequency waves which are isolated by buffer 73 and supplied to a two-pole switch 62 connected to transducers 50. Each transducer is also connected to a respective receiver 64, 66, to provide two input signals to a phase detector 68 whose output passes through a low pass filter 70 to a sample and hold circuit 72 and finally to an output amplifier 67, which provides the flow rate output signal.

The output signal from one of the receivers 66 is also provided to an amplitude detector 89; is filtered by a low-pass filter 75; and passes through the time gate 79 to a signal level output amplifier 77 which provides the installation circuit output signal. The output from amplitude detector 89 is also routed to an SR-type flip flop 84, as is the start pulse from the timing circuits 80. The output from the flip flop 84 passes through a low pass filter 86 to a size signal output amplifier 88 which provides the pipe size signal.

The output size signal magnitude from the processing circuit can be immediately used by a diameter calculating circuit or algorithm 63 to provide an accurate measure of the inside diameter, D, of the pipe. For example, in the depiction of FIG. 2, the transit time of the acoustic beam 54 yields, except for a correction associated with the finite width of the sensing head 18, three times the leg length of an equilateral triangle inscribed in a circle, thus indicating that the diameter is two times the leg length divided by the square root of three.

Those skilled in the transit-time measurement arts will appreciate that although the preferred circuit operates both transducers simultaneously, one could also choose to operate the transducers in an alternating mode having a first phase in which a first transducer transmitted while the second received and a second phase in which the second transmitted and the first received. Moreover, those skilled in the art will recognize that in cases where measurements from more than one pair of transducers are used to yield a single composite value of volumetric flow, the logical and mathematical processes that yield the composite value can be carried out in a number of known ways and may involve a wide variety of combinations of dedicated electronic hardware or general purpose electronic hardware operating under control of suitable software.

To aid in installation of the probe 10, the output from the carrier filter 80 is peak detected by an installation detector 89 and, after filtering by an installation low pass filter 75, amplified by an installation output amplifier 77 to provide an installation signal, which is preferably a DC signal, with a level responsive to the received electrical size signal strength. This DC signal is used by a local monitoring apparatus, which may be a visual display 90, to assist installation of the probe and can also be used remotely for maintenance or any other use. Although the preferred monitoring apparatus comprises a visual display that is removable from the sensor after installation is complete, one may note that many other sorts of monitoring apparatuses, including those that supply an audible or tactile output, may also be used with the invention.

A time gate 79 is provided to enable installation signals to be obtained only from a narrow range of acoustic transit times corresponding to a selected pipe size and insertion depth. It is anticipated that the time gate will have an initial, factory-set interval appropriate for a specified ID of a specified pipe. In some embodiments of the invention, if a gross error or mismatch is found during installation, the installer can use a mode control 87 to cause the time gate interval to reset to a different nominal pipe size, after which the installation could be re-attempted. It is expected that after several trials the appropriate size would be found and all necessary parts of the flow measurement equipment could then be re-programmed to match the newly established nominal diameter. Alternately, this process can be improved by defining a pipe size window and scanning through a range of transit time intervals as the probe is installed.

Preferred embodiments of the invention are used to assist in the installation of the probe, to measure both a raw flow signal value and a pipe size signal value, and to then employ a suitable flow measurement circuit means to calculate a volumetric flow output from the raw flow and size data. Although this approach is generally preferred, the reader will note that in some circumstances in which the pipe ID is known with acceptable accuracy beforehand, one could store a value of the pipe size signal (e.g., as a datum in a computer memory or as a manual calibration setting of a potentiometer) and a flow measurement circuit could receive that stored value and use that stored value in conjunction with one or more raw flow signals to calculate a volumetric flow rate. Those skilled in electronics will recognize that there are many possible ways to provide these calculations and that the flow measurement circuitry may comprise, without limitation, general purpose digital microcomputers and purpose-built analog circuitry.

Moreover, because the diameter can be easily re-measured from time to time, and because a decrease in the measured diameter can be indicative of dirt or scaling inside the pipe, one can store a value of the diameter in a suitable memory 68 at the beginning of a monitoring period and, later on, at the end of the monitoring period, compare the stored value with a then-current value. If the difference exceeds a selected threshold value, the apparatus can provide a suitable alerting or alarm message to a user of the apparatus to inform him or her that maintenance may be required. Those skilled in the art will recognize that one may make many choices as to the physical location and the type of memory that is used and that one could readily configure a measurement system in which the memory could be located at a central control room containing a computer programmed to track temporal variations in ID for a number of pipes in whatever flow system is being used. Moreover, it will be recognized that many means of making the comparison between the stored and current values are known in the electronic arts.

Those skilled in the art can now appreciate from the foregoing description that the teaching of the present invention can be implemented in a variety of forms combining a flow probe with a pipe size detector and installation aid. Therefore, while this invention has been described in connection with particular examples thereof, the true scope of the invention should not be limited since other modifications will become apparent to the skilled practitioner upon a study of the drawings, specifications and claims.

What is claimed is:

1. A sensor for measuring fluid flow in a pipe having a pipe axis, the sensor comprising at least two pairs of acoustic transducers disposed on at least one probe having a respective probe axis and insertable into the pipe to a respective probe insertion depth, each probe having a respective flow measurement direction transverse to the respective probe axis, each pair of the transducers associated with a second pair of the transducers, each pair of the transducers arranged to transmit and receive respective oppositely directed acoustic signals transverse to the respective flow measurement direction along a respective quasi-helical path having an opposite rotational direction from the quasi-helical path of that other pair of transducers with which said each pair is associated; the sensor further comprising signal processing circuitry for processing the acoustic signals from the at least two pairs of transducers to determine respective transit-times associated with each pair of transducers, for adding the transit-times of associated pairs to cancel effects of a rotary component of the flow and for providing a respective raw flow signal value representative of a component of the fluid flow along the respective flow measurement direction.

2. The sensor of claim 1 wherein the signal processing circuitry is further operable to generate from the acoustic signals at least one intensity output usable by an operator to determine that the respective probe insertion depth is within a selected insertion depth tolerance value of a respective desired insertion depth and to determine that the respective flow measurement direction is aligned with the pipe axis to within a selected rotational tolerance value.

3. The sensor of claim 1 comprising two probes insertable into the pipe to respectively selected insertion depths therein; each of the probes having a respective angular setting with respect to the pipe axis.

4. The sensor of claim 3 wherein one pair of the transducers is disposed on a first of the two probes and the second pair with which it is associated is disposed on the second of the two probes.

5. The sensor of claim 3 wherein two associated pairs of transducers are disposed on one of the two probes.

6. The sensor of claim 1 wherein the signal processing circuitry is operable to generate, from a transit-time component of at least one of the oppositely directed acoustic signals, a pipe size signal representative of an internal diameter of the pipe, the sensor further comprising a flow measurement circuit operable to combine at least one respective raw flow signal with the pipe size signal to provide an output representative of volumetric flow.

7. A method of measuring a component of fluid flow along an axis of a pipe when an overall fluid flow is characterized by having both the axial and a rotary component, the method comprising the steps of: a) generating, by means of a first pair of acoustic transducers spaced apart along the axis of the pipe, a first acoustic beam extending therebetween, the first acoustic beam reflected at least twice from an internal surface of the pipe, the first acoustic beam following a clockwise quasi-helical path along the axis of the pipe in the direction of the axial flow component; b) generating, by means of a second pair of acoustic transducers spaced apart along the axis of the pipe, a second acoustic beam extending therebetween, the second acoustic beam reflected at least twice from the internal surface of the pipe, the second acoustic beam following a counter-clockwise quasi-helical path along the axis of the pipe in the direction of the axial flow component; c) operating signal processing circuitry to determine respective transit-times associated with the two pairs of transducers; d) adding the two transit-times to cancel effects of the rotary component of the flow and e) providing a raw flow signal value representative of the component of the fluid flow along the axis of the pipe.

8. The method of claim 7 comprising additional steps of: f) determining, from the two transit times, an internal diameter of the pipe; and g) combining the internal diameter with the raw flow signal to provide an output representative of a volumetric flow rate of the fluid along the axis of the pipe.

9. The method of claim 7 wherein each of the two pairs of transducers is disposed on a respective probe.

10. The method of claim 7 wherein the two pairs of transducers are disposed on a single probe.

* * * * *